US011305138B2

(12) United States Patent
Bjorkquist et al.

(10) Patent No.: US 11,305,138 B2
(45) Date of Patent: Apr. 19, 2022

(54) IN SITU RESPIRATOR FIT TESTING

(71) Applicants: TSI Incorporated, Shoreview, MN (US); Aerosol Dynamics Inc., Berkeley, CA (US)

(72) Inventors: Daniel C. Bjorkquist, Shoreview, MN (US); Arantzazu Eiguren Fernandez, El Cerrito, CA (US); Kenneth Farmer, Lake Elmo, MN (US); Melissa Grose, Shoreview, MN (US); Susanne Vera Hering, Berkeley, CA (US); Gregory Stephen Lewis, Berkeley, CA (US); Steven Russel Spielman, Oakland, CA (US); David Workman, Shoreview, MN (US)

(73) Assignees: TSI Incorporated, Shoreview, MN (US); Aerosol Dynamics Inc., Berkeley, CA (US)

( * ) Notice: Subject to any disclaimer, the term of this patent is extended or adjusted under 35 U.S.C. 154(b) by 0 days.

(21) Appl. No.: 17/290,216

(22) PCT Filed: Oct. 31, 2019

(86) PCT No.: PCT/US2019/059234
§ 371 (c)(1),
(2) Date: Apr. 29, 2021

(87) PCT Pub. No.: WO2020/092821
PCT Pub. Date: May 7, 2020

(65) Prior Publication Data
US 2021/0316175 A1 Oct. 14, 2021

Related U.S. Application Data

(60) Provisional application No. 62/754,542, filed on Nov. 1, 2018.

(51) Int. Cl.
*A62B 27/00* (2006.01)
*G01N 1/22* (2006.01)
(Continued)

(52) U.S. Cl.
CPC .......... *A62B 27/00* (2013.01); *G01N 1/2273* (2013.01); *G01N 15/065* (2013.01); *G01N 2001/2276* (2013.01); *G01N 2015/0046* (2013.01)

(58) Field of Classification Search
CPC .... A62B 27/00; G01N 1/2273; G01N 15/065; G01N 2001/2276; G01N 2015/0046
(Continued)

(56) References Cited

U.S. PATENT DOCUMENTS 4,582,654 A 4/1986 Karnicky et al.
6,125,845 A 10/2000 Halvorsen et al.
(Continued)

FOREIGN PATENT DOCUMENTS

EP 3400077 B1 12/2020
WO WO-2020092821 A2 5/2020

OTHER PUBLICATIONS

"International Application Serial No. PCT/US2019/059234, International Search Report dated Jan. 17, 2020", 2 pgs.
(Continued)

*Primary Examiner* — Tri T Ton
(74) *Attorney, Agent, or Firm* — Schwegman Lundberg & Woessner, P.A.

(57) ABSTRACT

A system includes a first and second condensation particle counter, each counter having an inlet port, a growth column, and an optical element for counting particles detected at the respective inlet ports. The counters are configured to include a wick in which the wick is wetted by water. A differential pressure sensor is coupled to the first inlet port and coupled to the second inlet port. The sensor is configured to provide a pressure signal. A processor is coupled to memory and configured to receive the first signal, the second signal, and the pressure signal and generate an output corresponding to a ratio of the first signal and the second signal and correlate the ratio with the pressure signal. A housing is configured to receive the first counter, the second counter, the differential pressure sensor, the processor, and the memory.

13 Claims, 12 Drawing Sheets

(51) Int. Cl.
*G01N 15/06* (2006.01)
*G01N 15/00* (2006.01)

(58) Field of Classification Search
USPC .......... 356/36–50, 335–343, 432–444, 243.2
See application file for complete search history.

(56) References Cited

U.S. PATENT DOCUMENTS

| 9,683,962 B2 | 6/2017 | Janka |
| 2008/0137065 A1 | 6/2008 | Oberreit et al. |
| 2019/0201594 A1* | 7/2019 | Shelton, IV ....... A61B 1/00009 |

OTHER PUBLICATIONS

"International Application Serial No. PCT/US2019/059234, Written Opinion dated Jan. 17, 2020", 4 pgs.
"International Application Serial No. PCT/US2019/059234, International Preliminary Report on Patentability dated May 14, 2021", 7 pgs.

* cited by examiner

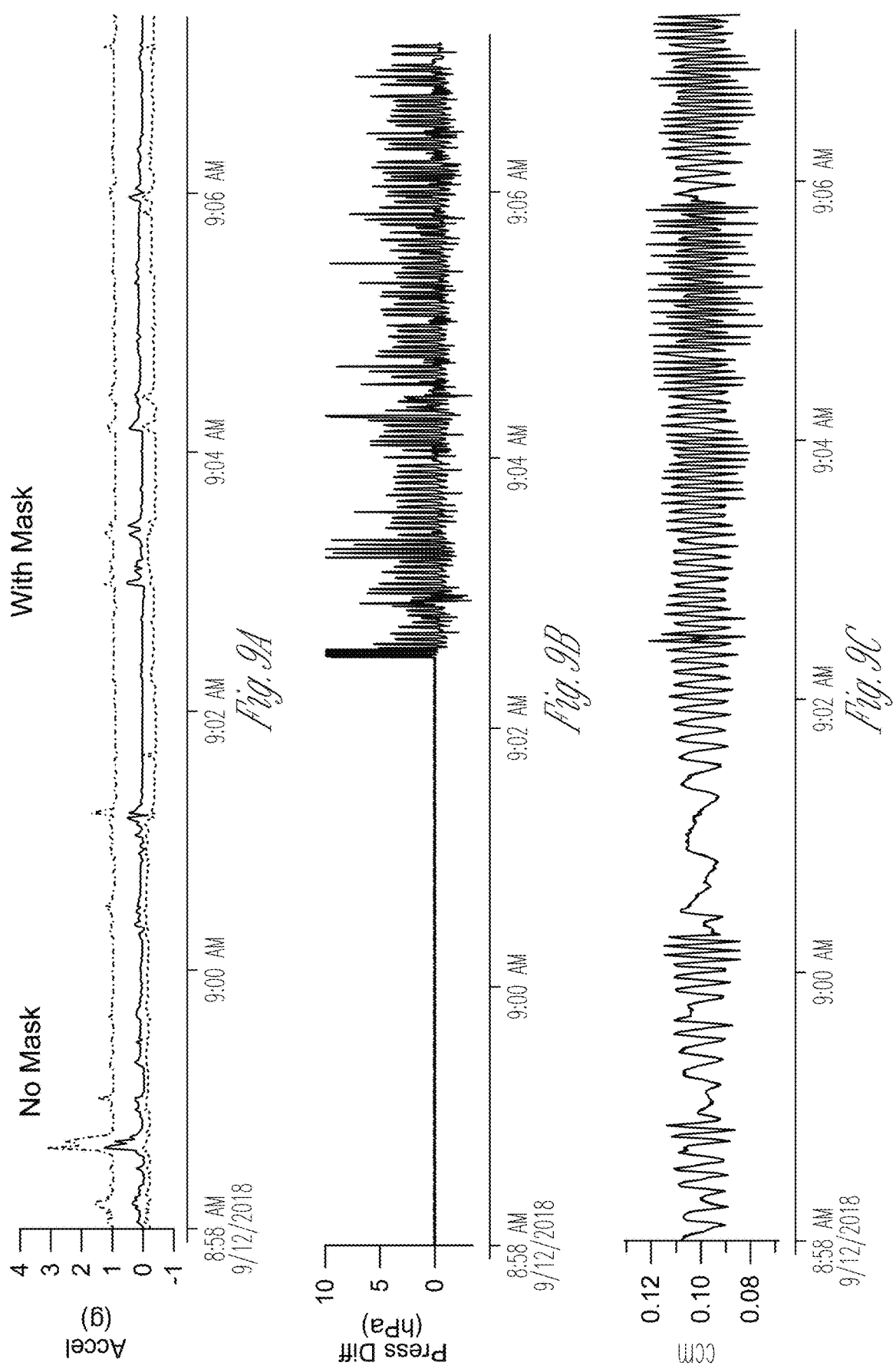

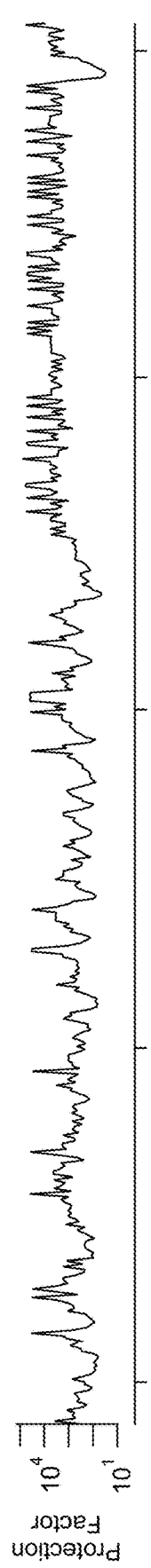
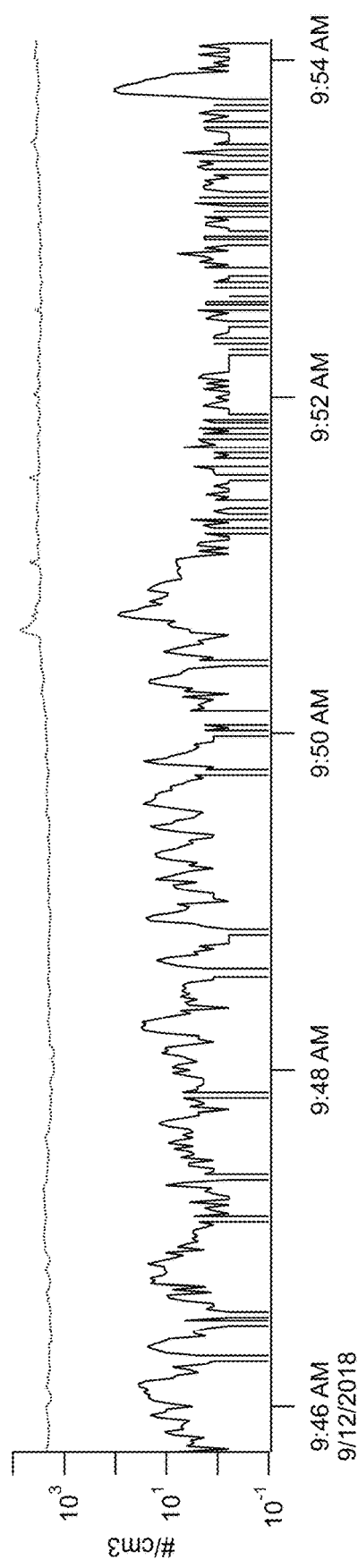
Fig. 10D
Fig. 10E

IN SITU RESPIRATOR FIT TESTING

CLAIM OF PRIORITY

This patent application is a U.S. National Stage Filing under 35 U.S.C. 371 from International Application No. PCT/US2019/059234, filed 31 Oct. 2019, which claims the benefit of priority of U.S. Provisional Patent Application Ser. No. 62/754,542, filed on 1 Nov. 2018, the disclosures of which are hereby incorporated by reference herein in their entireties.

STATEMENT REGARDING FEDERALLY SPONSORED RESEARCH OR DEVELOPMENT

This invention was made with government support under contract HDTRA1-16-C-0065 awarded by Defense Threat Reduction Agency (DTRA). The government has certain rights in the invention.

TECHNICAL FIELD

This document pertains generally, but not by way of limitation, to measuring airborne contaminants associated with a respiratory mask.

BACKGROUND

Emergency response personnel and military personnel use respirators for protection from airborne contaminants. Yet the effectiveness of these respirator depends not only on the quality of the filters employed, but also on the integrity of the fit of the respirator to the face of the user.

Technology for testing the fit of a respirator is inadequate.

SUMMARY

An example of the present user matter includes a dual-channel, ultrafine particle counter for in situ respirator fit testing. In situ respiratory fit testing is conducted with the respirator affixed to the user, and in some examples, this is referred to as on-person fit testing.

One example is directed to measuring the degree of protection from filterable, airborne contaminants afforded by a respirator mask while it is being worn by a user. One example assesses the fit of the mask on the user, as well as the effectiveness of the mask's filters. One example is a wearable device configured to measure parameters while the user is physically active. One example measures and records selected indices of the user's activity level during respirator testing, thereby facilitating the study of the circumstances, or types of activities, that may degrade the respirator performance.

The quality of respirator fit may depend on the activity level of the user. An example of the present user matter is directed to evaluating the level of protection afforded by the mask in use. Such evaluation can be addressed through a wearable sensor.

One example includes a wearable device to assess the in-use effectiveness of the respirator mask. The degree of protection can be determined using a water-based condensation particle counter that measures the number concentration of airborne particles immediately outside the mask, and the concentration inside the mask, within the user's breathing area. These airborne particles act as a tracer for the amount of unfiltered air that penetrates the mask. A ratio of the number particle number concentration outside the mask to that inside the mask is called a "protection factor".

An example of the present user matter can be configured for measuring the number concentration of ultrafine, airborne particles, namely those with diameters ranging from approximately 10 nm to about 200 nm. These ultrafine particles are naturally highly abundant in the atmosphere. By enumerating their concentration immediately outside and inside of the respirator mask, it is possible to verify protection fitness factors as high as 105 over time periods of a few seconds, using ambient particles as the challenge. Thus, measurements can be done using ambient particles, without the need to generate a cloud of particles for testing.

Ultrafine airborne particles require condensational growth to enable their detection at the single particle level. One example of a condensation particle counter can detect ultrafine particles as small as 20 nm. One example of a commercially available condensation particle counter is designed for static testing, with the user seated and tethered to a desktop instrument. It is not suitable for measurements while the user is running, jumping, or otherwise physically active.

One example of the present user matter includes a wearable, dual channel, water-based condensation particle counter configured to measure ultrafine particle concentrations both inside and outside of the respirator mask while the user is physically active. One example has two channels, permitting simultaneous measurement of particle concentrations inside and outside of the respirator mask.

One example of the present user matter includes an accelerometer to assess the activity level of the user during measurement. One example of the present user matter incorporates a differential pressure sensor to detect the pressure drop across the mask, which is an indication of the nature and rate of the user's breathing. One example of the present user matter provides active flow monitoring of each of the two measurement channels. In one example, all these data are recorded in an on-board memory, with a common time stamp, so that leakage, when detected, can be correlated to the user's activity and breathing. Unlike the alcohol-based condensation particle counters of the prior art, one example of the present user matter uses a water-based condensation method, thus eliminating human exposure to this organic solvent, as well as the need for special supply item. Further, one example of the present user matter is battery powered, motion-tolerant, and compact. It can be mounted on the user's vest, belt or back pack. It may be worn by the user during measurement, enabling active, on-person measurement.

The present inventors have recognized, among other things, that a problem to be solved can include measuring respirator fit when worn by an active user. The present user matter can help provide a solution to this problem, such as by measuring particle counts both in the ambient environment and in the filtered-air environment under the respiratory mask as well as correlating particle count measurements with a measure of user activity level.

Each of these non-limiting examples can stand on its own, or can be combined in various permutations or combinations with one or more of the other examples.

This overview is intended to provide an overview of user matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

An example of the present subject matter provides simultaneous measurement of ultrafine particle number concentrations in two channels, within a compact, battery operable, motion-tolerant instrument. The technical approach for ultrafine particle detection uses a motion-tolerant, water-based particle condensation method. One example of such a method is described in U.S. Pat. No. 9,610,531 (Hering et al, 2017), which in turn is based on the three-stage laminar flow water condensation technology described in U.S. Pat. No. 8,801,838 (Hering et al, 2014). It uses water, rather than alcohol, to add condensate to ultrafine particles to form optically detectable droplets. Additionally, water vapor is captured internally, thereby providing sustained operation without liquid replenishment, and without a liquid reservoir. Units based on this technology are impervious to jostling, shaking or orientation; a feature that results from the elimination of a liquid reservoir.

One example of the present subject matter includes a wearable respirator protection assessment system. One example is configured for respirator fit test measurements.

One example has two flow channels, one which samples from the airspace inside the respirator mask, and one that samples the ambient air immediately outside the mask. In one example, the user's breathing space inside of the respirator mask is accessed via the respirator drink tube. For example, particles can be measured using a flexible tube coupled to a drink tube port of the respirator.

The flow in each channel is configured to pass through a growth tube where ultrafine particles are enlarged through water condensation to form droplets which are subsequently counted by the optical detector. This provides simultaneous detection of ultrafine particles inside, and immediately outside of the mask.

A ratio between these two values represents a measure of the instantaneous protection afforded by the respirator mask. In one example, data are reported every second, yielding second-by-second readings of this protection factor.

Figure 1:
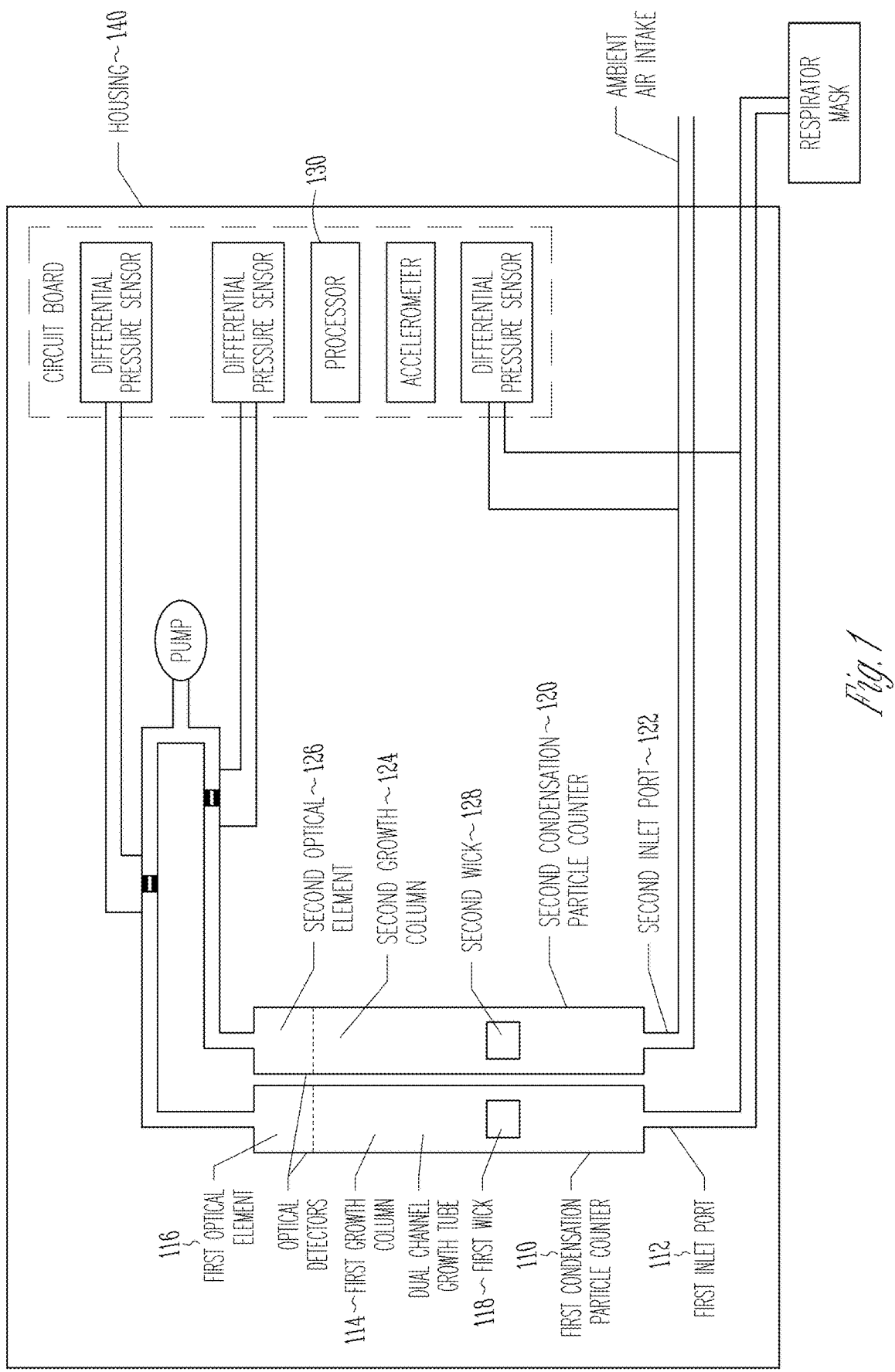
FIG. 1 illustrates a schematic of a system illustrating dual channel particle condensation growth tubes, pair of optical detectors, differential pressure measurements and accelerometer, according to one example.

In addition to these particle concentration measurements, one example of the present subject matter also monitors indicators of (1) how deeply and rapidly the user is breathing and (2) how much the user is moving. These factors can facilitate in investigation of the efficacy of a respirator mask, as the fit can depend on the user activity. The user's breathing is indicated by the differential pressure sensor to detect the pressure drop across the mask, as illustrated in FIG. 1. The filters through which the air passes create a pressure drop, and this pressure drop depends on the rate of that air flow. Thus, the pressure difference between the inside and outside of the mask fluctuates with each breath, and the extent of that fluctuation depends on how rapidly the user draws in air. Thus, this measurement indicates the nature and rate of the user's breathing. In one example of the present subject matter, this parameter is recorded at the rate of 10 Hz, so that individual breaths can be tracked.

The user's motion and orientation can be monitored by the onboard accelerometer, which detects acceleration in each of three coordinates (x, y and z directions) at the rate of 50 Hz. This data set is sufficient to determine if the user is still, walking, running, jumping, etc. All these data are recorded on-board, with a common time stamp, so that leakage, when detected, can be correlated to the user's activity and breathing.

One example of the present subject matter incorporates active flow monitoring of each of the two measurement channels. The flow exiting each optics head passes through a flow metering orifice, with pressure transducers that are calibrated to provide a reading of the flow in each channel. This provides active flow measurement in each of the two channels on 1-sec time scales. This maintains accuracy in the particle concentration measurement, which is the ratio of counts to the volume of air sampled, should heavy breathing temporarily alter the flow split between channels. These measurements are illustrated in FIG. 1.

FIG. 1 illustrates a representation of first condensation particle counter 110 having a first inlet port 112, first growth column 114, and first optical element 116, first wick 118 and illustrates a representation of second condensation particle counter 120 having a second inlet port 122, second growth column 124, second optical element 126, and second wick 128. FIG. 1 also illustrates processor 130 and housing 140, according to one example.

One example of the present subject matter utilizes motion-tolerant particle condensation technology such as that in U.S. Pat. No. 9,610,531 in a dual channel water condensation growth tube and pair of miniature optical detectors, as shown in FIG. 2.

The dual channel growth tube has three stages, each at separate temperatures, spanned by a continuous wick that transports water via capillary action among the stages. The first stage, referred to as the "conditioner", cools and humidifies the incoming flow. The second stage, called the "initiator", has warm, wet walls that add water vapor to the flow, thereby creating the supersaturation required to initiate condensational growth of ultrafine particles. The third stage, called the "moderator", cools the flow and recovers water vapor while maintaining supersaturated conditions. Water recovered within the conditioner and moderator stages is transported via capillary action to the initiator where it evaporates to create the supersaturation.

Figure 2:
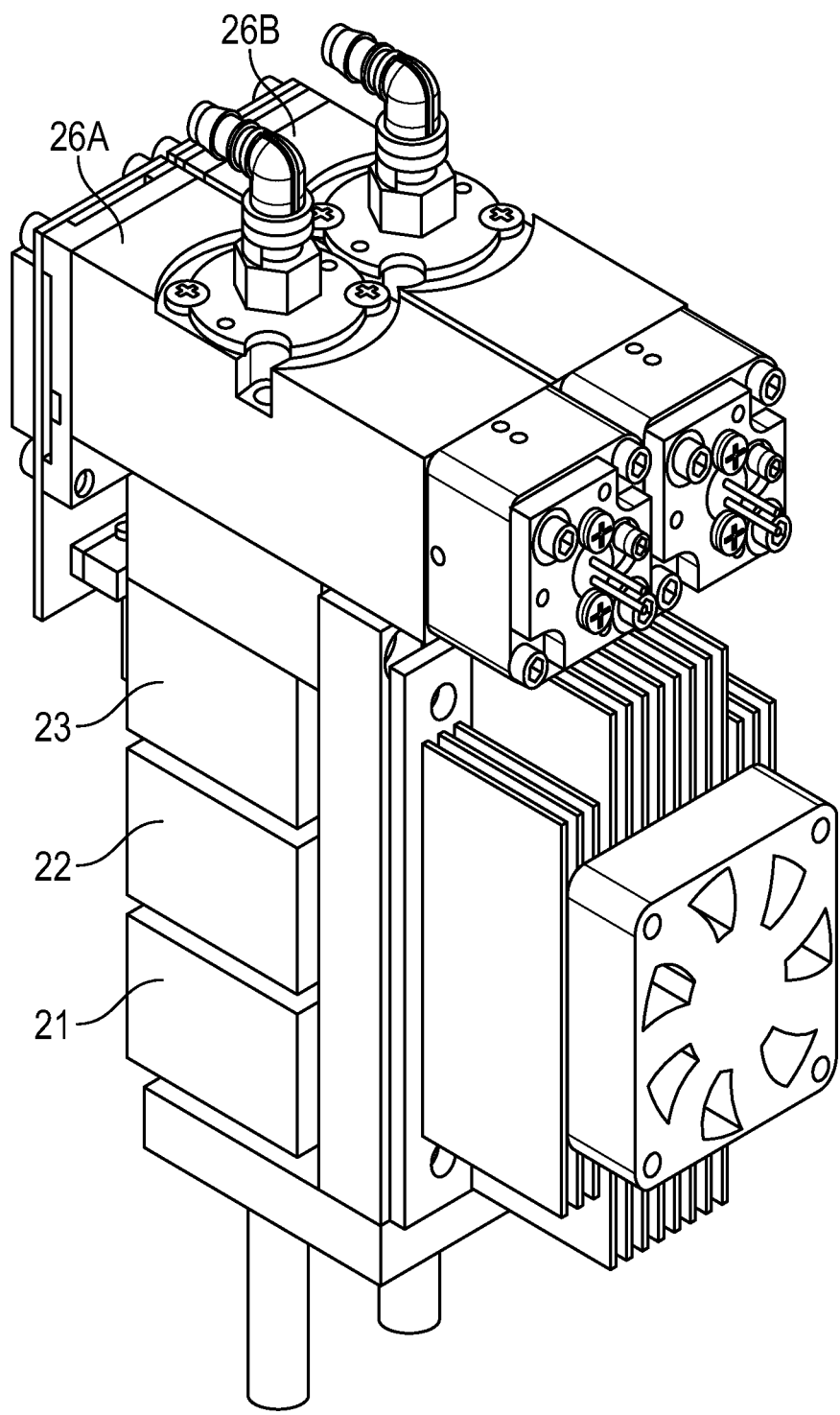
FIG. 2 illustrates a view of a growth tube and optical detector, according to one example.

FIG. 2 illustrates some design aspects to enable miniaturization in a dual channel design. The three stages are seen by the blocks 21, 22, and 23, while the optics heads 26A and 26B sit on top. The instrument uses three thermal electric devices, each operated as a heat pump with a common heat sink. The air flow 100 cc/min per channel. The size of thermal electric devices, and the coupling between stages, can be tailored to reduce the power consumption. An optical detector can be a miniaturized version of a forward scattering detector. While the overall focal length was maintained, the width of each optics head can be reduced from 1.3 inches to 0.75 inches. The laser module can be configured to allow the laser to allow alignment while both optical detectors are mounted in place, i.e. side by side. The electronics can be configured to include the laser control together with the photo diode detector electronics on a single board that mounts to the optics head. In one example, the optics are configured as a complete module, which can be easily replaced.

One example includes a folded circuit board to house selected components and the electronics in a compact package. The display and microprocessor chip are on one board mounted at the top of the instrument. This connects via an edge connector to the power board, which has micro-connectors for fans, temperature sensors, thermal electric devices, pumps, etc, as well as USB and power connectors. This allows a thinner and more ergonomic package.

Figure 3:
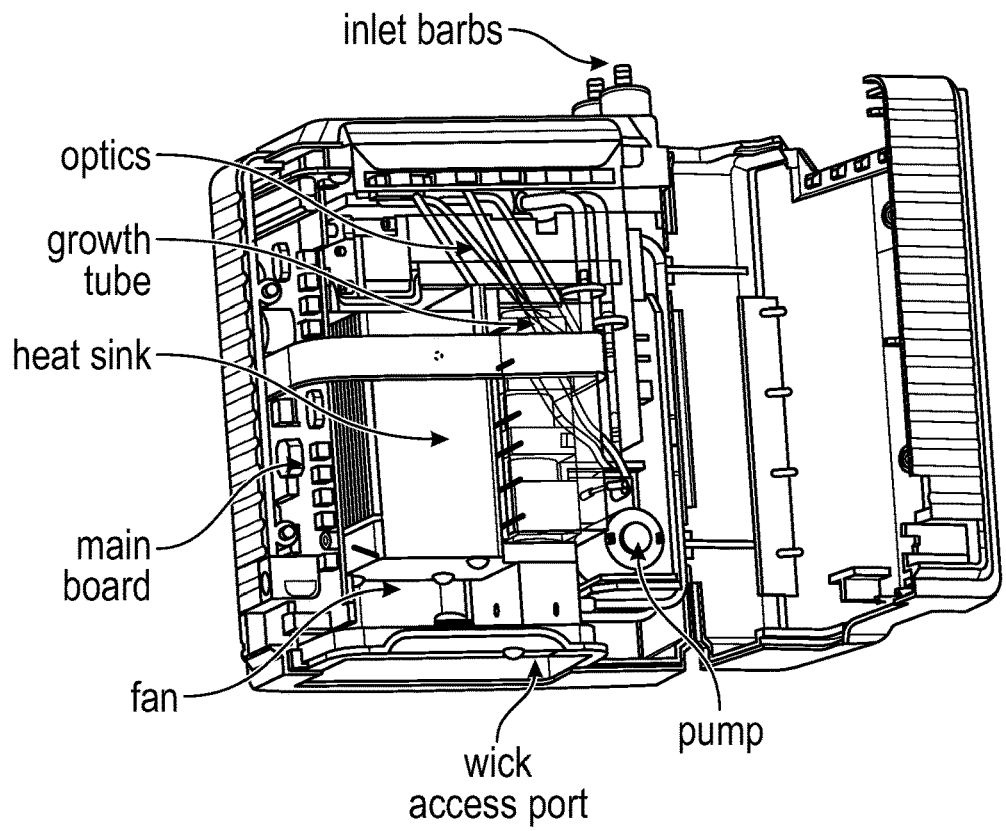
FIG. 3 illustrates a view of a system showing internal components, according to one example.

Further size reduction can be achieved through careful placement of components, taking into account electrical cabling and pressure sensor connections. FIG. 3 is an internal view of one example in a case, showing the mounting of the internal components in its case. In this example, the power circuit board is along the left side, and connects to the display board at the top. A ribbon cable runs between the main board and the optics board. Various micro-connectors on the power board are mounted on the side to provide a straight run to the components.

Figure 4A:
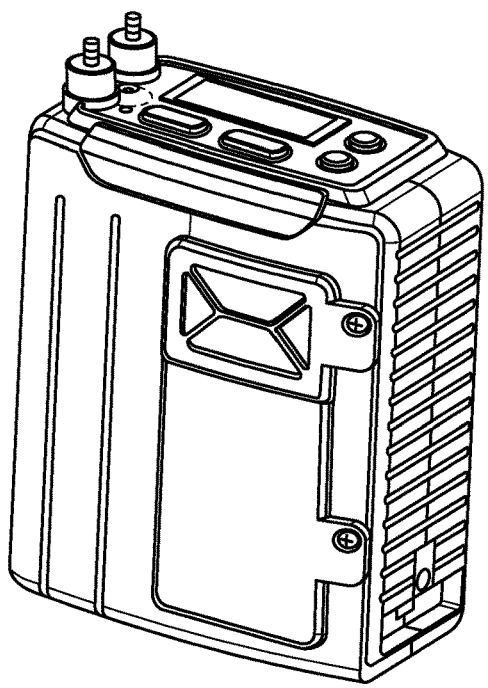
FIGS. 4A and 4B illustrate external views of a system, according to one example.
Figure 4B:
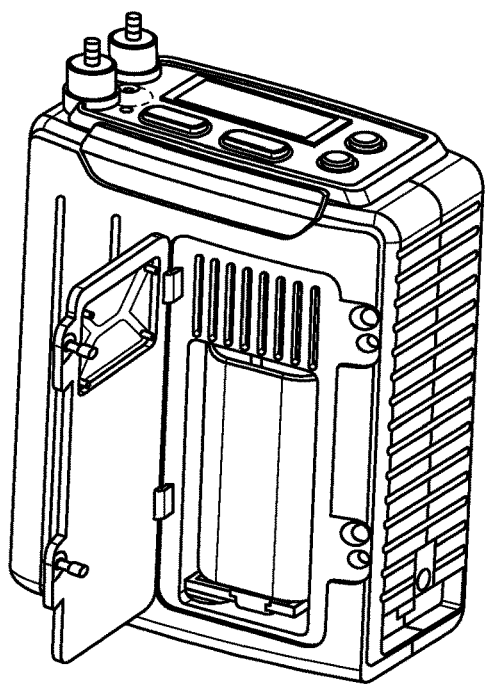
Figure 5:
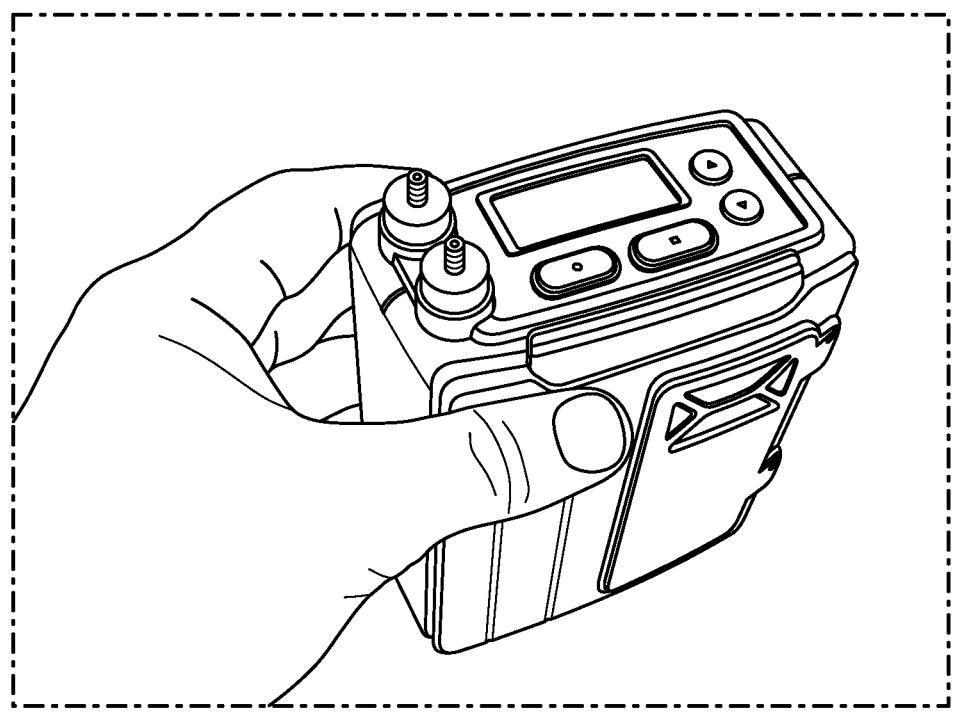
FIG. 5 illustrates a view of a system, according to one example.

FIG. 4 shows the outside view of one example of the present subject matter. The ventilation intake is on a front surface, and is protected by a low-efficiency filter. Ventilation flow exhausts out a bottom surface. The battery door is also on the front surface, and is easily accessible. A pigtail allows the battery to be swapped. A display is oriented on a top surface and remains visible when the device is installed in a pouch or while held by an operator. The assembled system is shown in FIG. 5. The battery is accessible through the door on the outside of the case. The air intake is through the battery door, and includes a field-replaceable dust filter. The size is 860 cm$^3$, and the weight, with battery, is 780 g.

Figure 6:
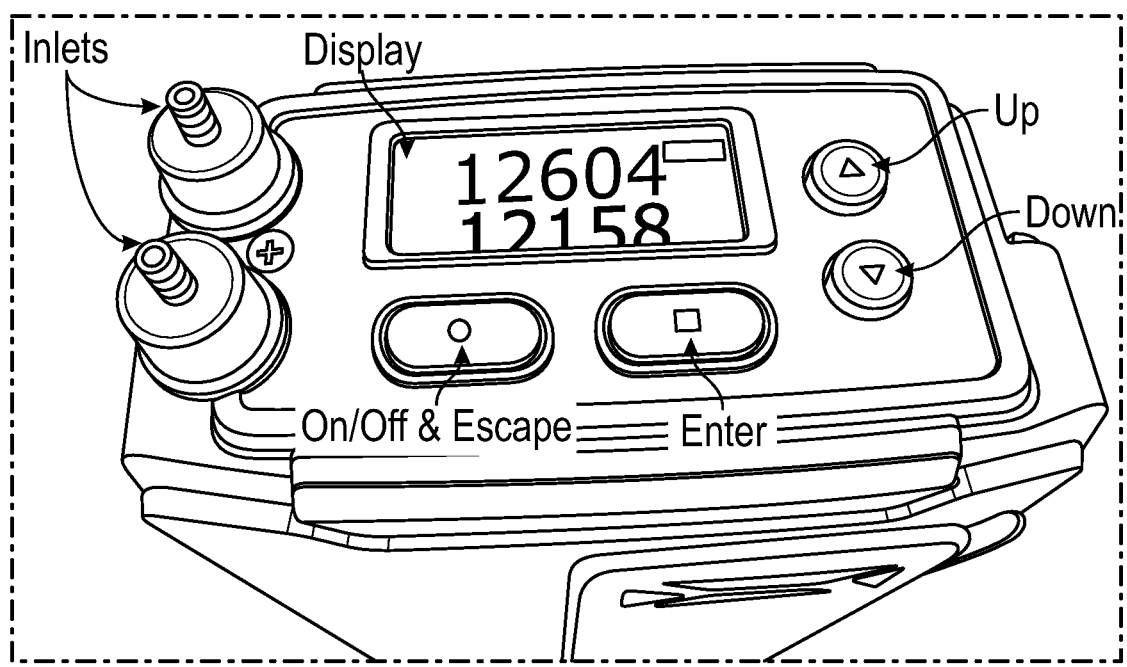
FIG. 6 illustrates a view of a system including a display and user interface buttons, according to one example.

The user interface is through the display (screen) and buttons mounted on the top of the unit, as shown in FIG. 6. The software is menu driven, with up/down and enter and escape buttons for navigation. The power (on/off) button turns power on and off when depressed for more than 3 seconds, and otherwise acts as an escape to carry the user up one level in the menu. The user interface has a main screen and three subscreens, as listed in Table 1. From the main screen the user may select "counts", which gives the option of "concentration" or "ratio". An example of a concentration screen is shown in FIG. 6, and displays the number concentration measured by each channel. In this example both lines are sampling from the ambient air, and thus concentration readings are comparable. The ratio sub-screen displays the ratio in counts between these two channels, and is useful for examining the precision between the two channels (i.e. a ratio within 1.0±0.1) or for looking at a real-time protection factor, calculated as a running 5-sec ratio of the average ambient particle concentration divided by the average in-mask concentration. The 5-second interval can be used for averaging, and in one example, is stored in a variable, and can be selectable through a laptop or from a screen.

The "fit test" screen allows the user to run a pre-programed fit test. The software can be configured to allow the test protocol to be programmed through a laptop connected to the instrument. The operator presses "enter" to start, and can terminate at any point by pressing "escape". In one example, the screen shows the Pass/Fail status and Protection Factor, at each step, and the cumulative (harmonic mean) Protection Factor at the end of the test. A summary screen displayed at the conclusion shows the protection factor at each step.

One example of the present subject matter includes an on-board data storage and Wi-Fi capability for storing and transmitting data in real time. The Wi-Fi channel sends data to a router, which then communicates to a laptop computer. These data is stored in a text file, and read via a suitable program (such as Python) to make these data readable by the laptop. The on-board storage includes a flash memory, and is downloaded to a laptop via a USB connection. In one example, both the Wi-Fi and flash memory data share the same file structure.

Figure 7A:
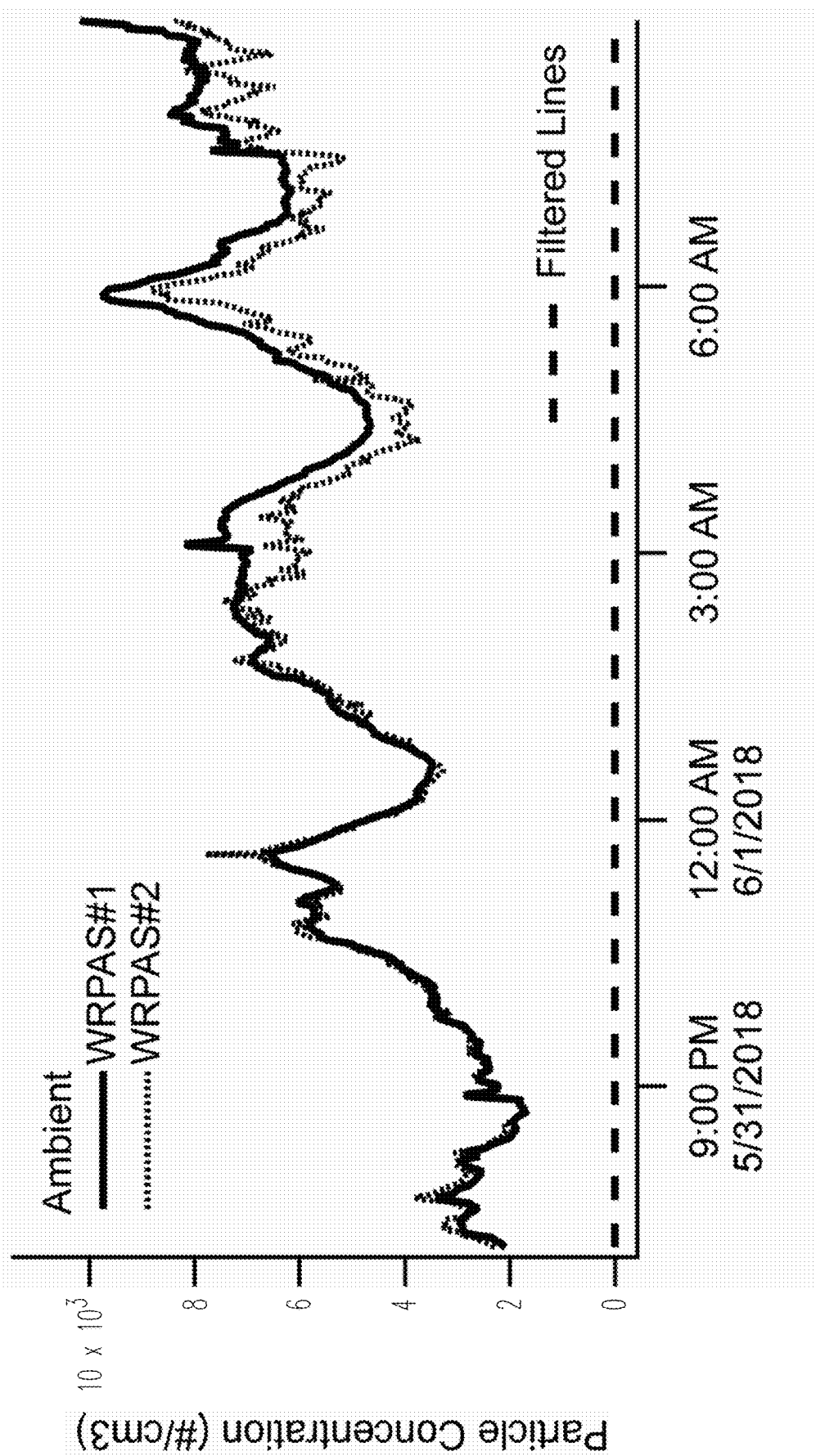
FIG. 7 illustrates graphs of zero counts, that is particle counts detected with an absolute filter on one of the sampling lines over a 12-hour measurement period, according to one example.
Figure 7B:
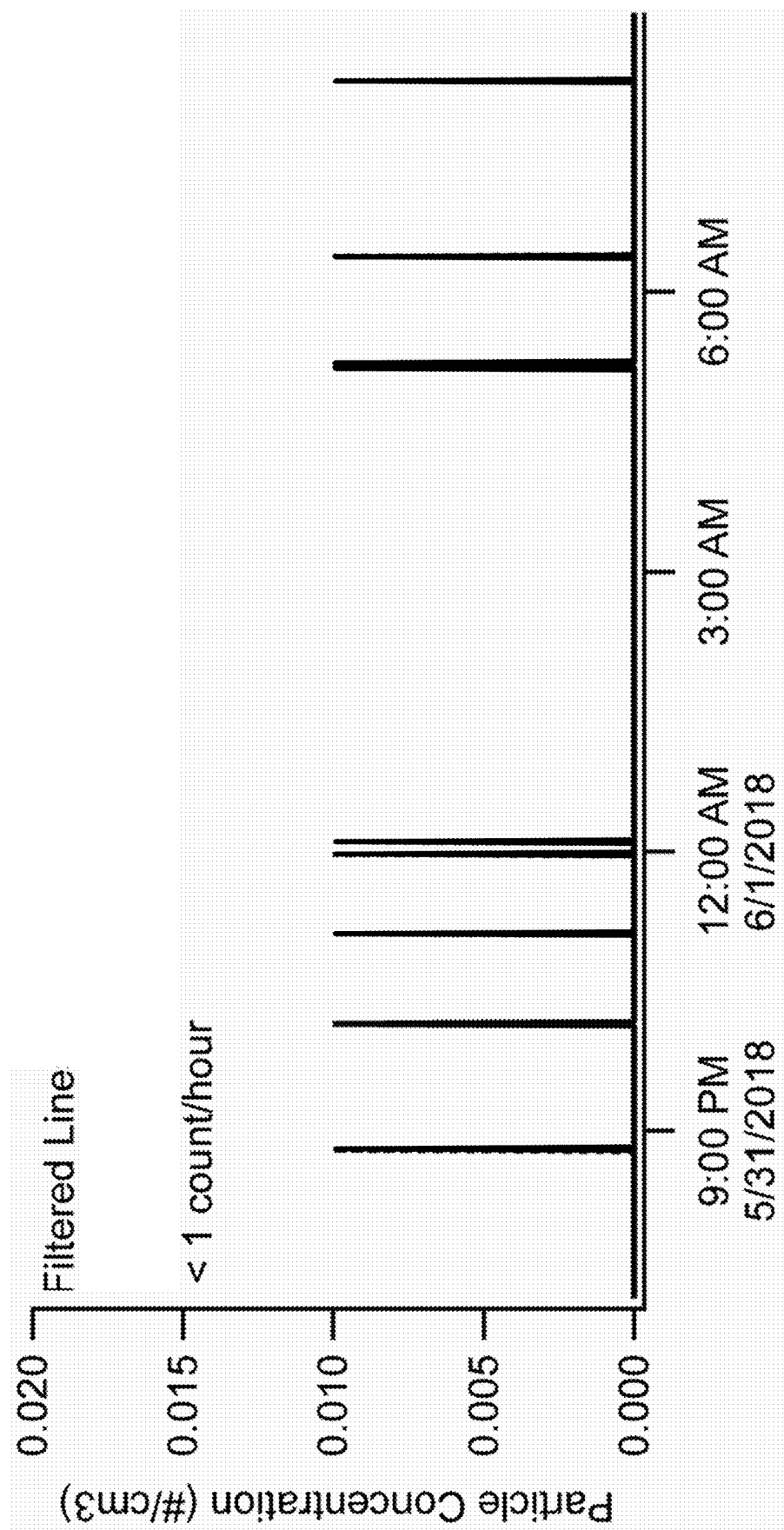

Measurement of Protection Factor entails measuring very low particle concentrations, in other words the false count must be low. This can be tested by operating the pair of channels for an extended duration (such as overnight) with a filter on one line, while the other line samples ambient air. An example of results are shown in FIGS. 7A and 7B. While the ambient particle concentrations fell in the range of 2,000-10,000/cm$^3$, the filtered air line yielded less than 1 count/hour. Even if this one count occurred during a 30-s reading of the protection factor, the corresponding in-mask concentration would be 0.02/cm$^3$, and the indicated protection factor (at ambient concentration of 2,000/cm$^3$) would be 105.

Figure 8A:
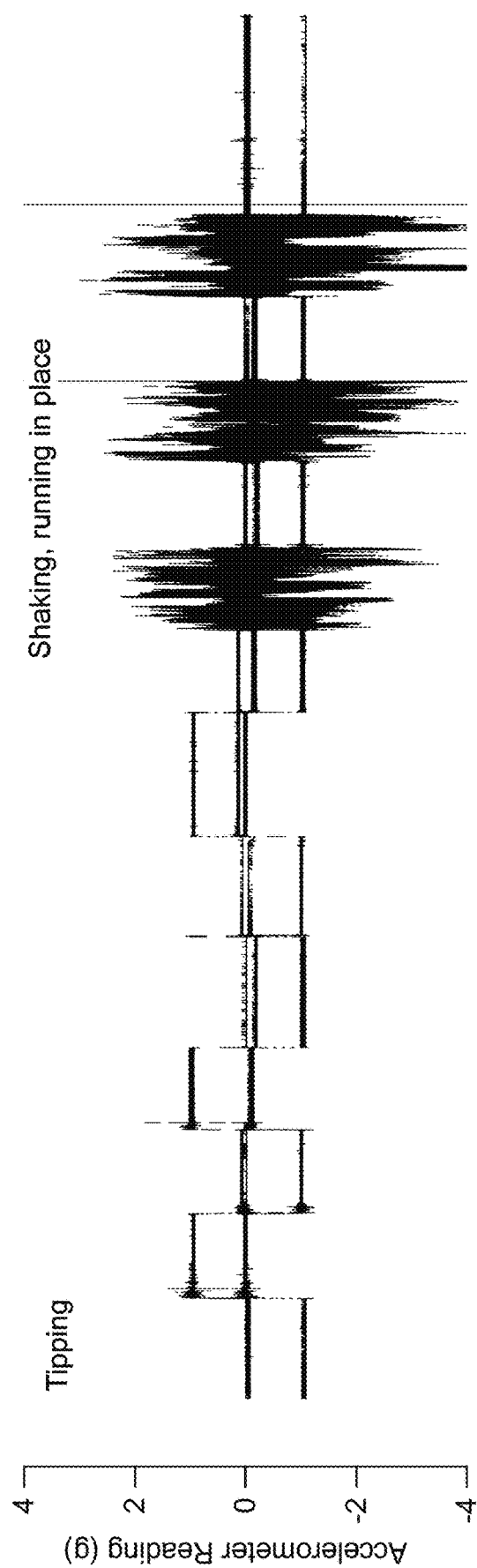
FIG. 8 illustrates graphs of ambient particle concentrations measured by an example system while being tipped and while in motion, according to one example.
Figure 8B:
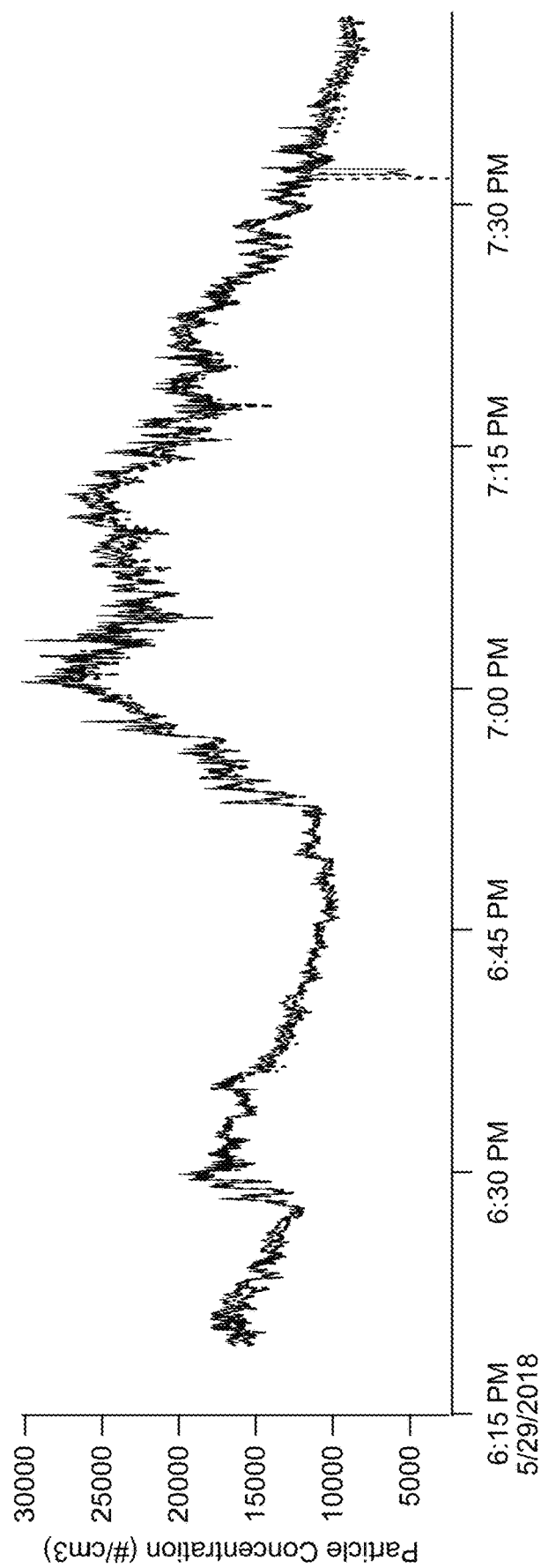

Laboratory test data with one example of the present subject matter is shown FIGS. 8A and 8B. One sampling line can be connected to a respirator, and the other sampling ambient air, as would be done for assessing the protection factor. Shown are the acceleration, as measured by the on-board sensor, the number concentration in each channel as well as that from a nearby benchtop condensation particle counter, and the resulting protection factor (calculated as a 5-sec running average). With the respirator in place, the protection factor indicated by the Level 2 system varied from 350 to 3,500, with a mean of 4,900 while the user was standing, and 1,100 while the user was jumping. When the respirator was removed the protection factor was 0.92, indicating measurement within 10% of ambient particles by both channels.

FIGS. 9A-9E shows results for on-person testing, in which the respirator is mounted on a vest worn by a user. The results here can depict testing conducted during Chemical Biological Operational Analysis (known as CBOA), with the user donning the mask midway through.

Figure 9D:
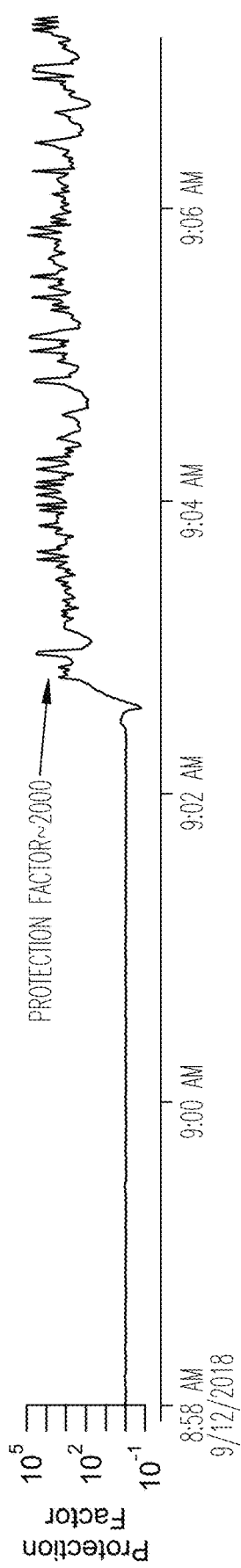
FIG. 9 illustrates graphs of on-person testing, with the user putting the mask on half-way through the data shown, according to one example.
Figure 9E:
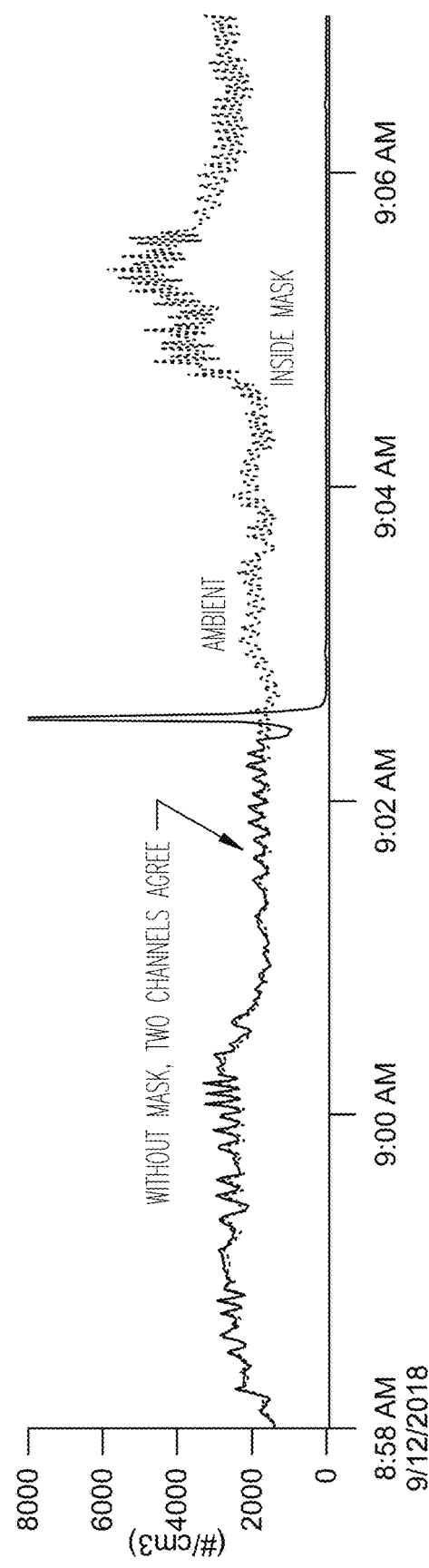

Accelerometer data in each of the x, y, and z axis are shown in FIG. 9A, which for this test was mostly small. The 1-g reading on the one trace indicates gravity, and the orientation of the unit. Pressure differential data, that is the difference in air pressure from outside, and inside of the mask, is shown in FIG. 9B. In this example of FIG. 9, the pressure difference is near zero until shortly after 9:02 AM, when the subject donned his respirator mask. Subsequent pressure variations, recorded at 10 Hz, are due to the pressure drop, and over pressure, created by the user's breathing through the respirator. FIG. 9C shows the flow readings for each channel, which vary by 5%, and these are mostly due to pulsations introduced by the pump, rather than from the users breathing. The data is corrected for these flow variations. FIG. 9D shows the 1 Hz protection factor, calculated as the ratio outside/in-mask particle concentrations reported each second. When particle counts inside the mask are 0, we assume a concentration corresponding 0.5 counts, as to prevent infinite protection factors. Before putting on the mask, reported protection factors are around 1, indicating agreement between channels. With the mask, the protection factor was around 2000.

Figure 10A:
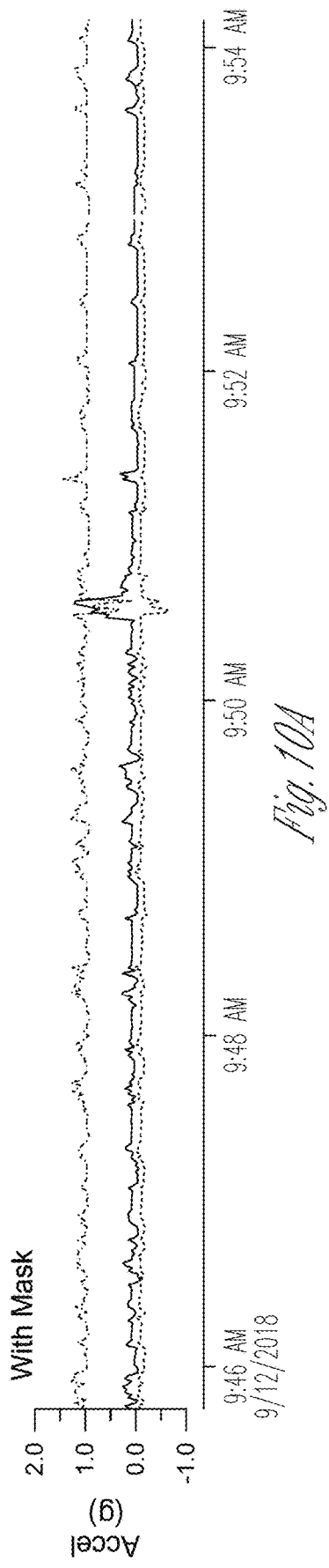
FIG. 10 illustrates graphs of on-person testing while the mask was worn throughout the measurement period, according to one example.
Figure 10B:
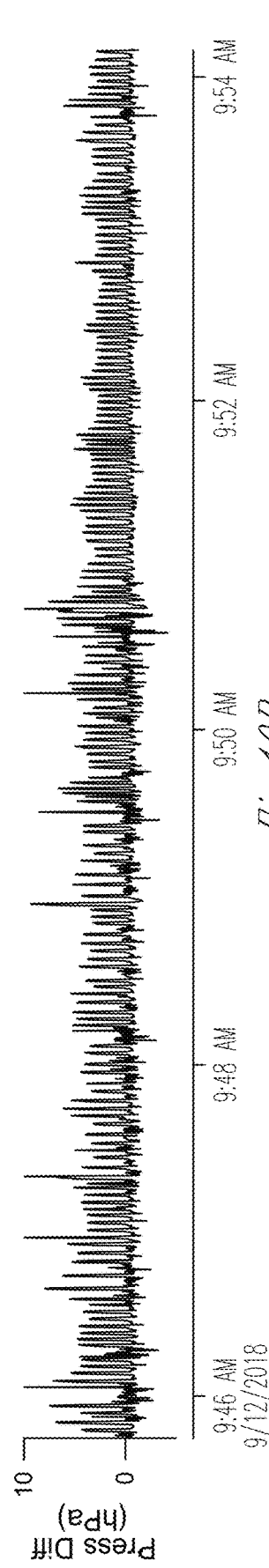
Figure 10C:
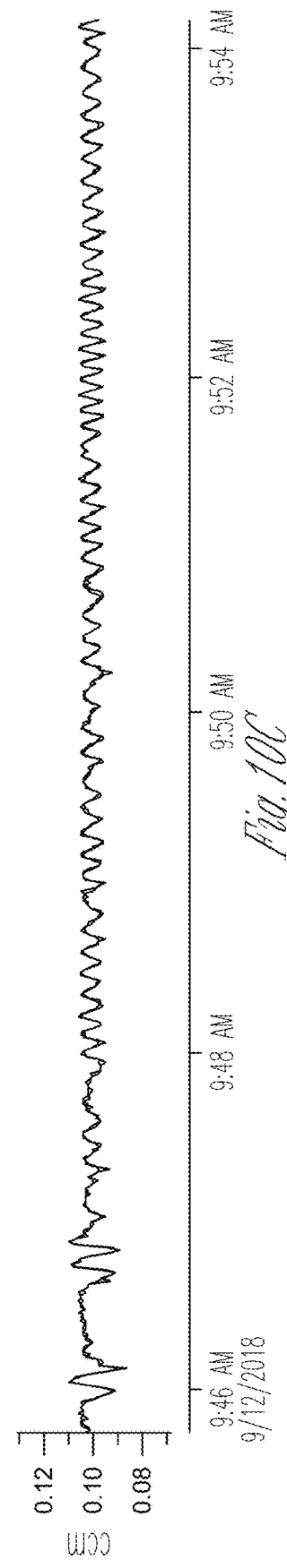

Data from later on in the same test as shown in FIG. 10. The figure shows on-person testing conducted during CBOA, when a user wears the mask throughout.

Here, considerable variation is evident in the protection factor during the user's activities, with 1-sec averaged values ranging from 30 to 50,000. The plots, marked FIGS. 10A, 10B, 10C, 10D, and 10E, depict the type of data that can be obtained with one example of the present system. Further, the data shows that there is variability in the mask performance as it is worn.

Additional

One example of the present subject matter includes a wearable device to measure the protection afforded by a respirator while the user is physically active, through simultaneous measurement of the penetration of unfiltered air into the users breathing space, and further through simultaneous detection and recording of the user's activity level as indicated by breathing rate and accelerometer readings. In a miniaturized, battery-powered and wearable unit, the system couples measurement of the respirator protection factor simultaneously with measurement of key indicators of the users activity level. Further, one example uses water rather than alcohol to enable ultrafine particle detection, and combines two channels in a single unit. The wearable, dual channel, water-based, ultrafine particle counting, incorporating accelerometer sensor and inside/outside mask differential pressure sensor provides the opportunity to better understand in-use respirator fit and integrity.

Selected features of one example include:
  dual channel for simultaneous detection inside, and outside of the mask
  ~7 nm particle detection
  operable on distilled or tap water (no alcohol required)
  ±10% precision between channels
  1 Hz resolution on protection factor
  motion-tolerant to ±2 g's
  greater than 4 hour of battery operation
  active flow monitoring of each channel
  on-board, 50 Hz accelerometer readings (indicative of user motion)
  on-board, 10 Hz measurement of pressure difference across the mask (indicative of breathing)
  internal data logging
  data transmission over Wi-Fi
  includes a standard fit test
  780 g, 860 cm$^3$ package
  carrying pocket to enable mounting on a vest, on a belt strap, or in a backpack.
  software receives, processes and displays data from one or more units as it is received.
Performance data show:
  lower detection threshold of 7 nm,
  comparable values for ambient particle numbers concentrations to that obtained by commercial condensation particle counters
  insensitivity to orientation
  insensitivity to shaking, and ±2 g accelerations
  false count rate of less than 1/hour
  demonstrated capability to measure inside, and outside of a respirator mask, including with the user in motion.

In one example of the present subject matter uses two channels with each channel having separate growth tubes and separate optics. Unlike systems using a single channel and ports selected by a valve or switch, the two ports can be simultaneously measured. One example uses a common thermal unit (heating and cooling).

The processor of one example of the present subject matter can be configured to process the pressure signal from the differential pressure sensor and discern breathing rate and associated activity.

Wick materials can include Nylon, high-density polyethylene resin (HDPE), low-density polyethylene resin (LDPE), polyethylene, stainless steel, sintered material, ceramic, polyvinylidene fluoride (PVDF), nitrocellulose, polytetrafluoroethylene (PTFE), or other hydrophilic material. The wick is fully wettable, designed to transport by capillary action, small pores (sub-micron), uniform pores.

Wick is wetted by distilled water or tap water. No reservoir required for make-up water—uses a self-sustaining water wick.

TABLE 1

| Menu item | Secondary Screen | Action |
|---|---|---|
| COUNTS | Concentration | Displays particle number concentration in each channel |
| | Ratio | Disphys ratio in particle concentrations between channels |
| FIT TEST | CBRN - press enter to start | Proceeds through the CNBR, fit test, reporting PASS/FAIL status and Fit Factor at each step, and the overall PASS/FAIL and Fit Factor. A final screen summarizes the results. |
| | Active - press enter to start | Displays 5-sec averaged Protection Factor until user pushes "escape" |
| STATUS | General | Set clock, screen contrast, enable backlight |
| | Data Mode | turn Wi-Fi on/off, switch on-board storage on/off clear memory |
| | Battery | shows time remaining |
| | Accelerometer | display current accelerometer readings |
| | Advanced | display flows, pressures, temperatures |

NON-PATENT LITERATURE

Hering, S. V., Lewis, G. S., Spielman, S. R. (2018) A MAGIC Concept for Self-Sustained, Water based, Ultrafine Particle Counting. Aerosol Science and Technology, accepted, in press.

Hering, S. V., Speilman, S. R., Lewis, G. L. Moderated, water-based condensational growth of particles in a laminar flow. Aerosol Science and Technology 48:401-40, 2014.

Various Notes

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive user matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system comprising:
   a first condensation particle counter having a first inlet port, a first growth column, and a first optical element for counting particles detected at the first inlet port, the first condensation particle counter configured to provide a first signal corresponding to the particles counted at the first inlet port;
   a second condensation particle counter having a second inlet port, a second growth column, and a second optical element for counting particles detected at the second inlet port, the second condensation particle counter configured to provide a second signal corresponding to the particles counted at the second inlet port;
   wherein the first condensation particle counter and the second condensation particle counter are configured to include a wick in which the wick is wetted by water;
   a differential pressure sensor coupled to the first inlet port and coupled to the second inlet port, the sensor configured to provide a pressure signal;
   a processor coupled to memory and configured to receive the first signal, the second signal, and the pressure signal and generate an output corresponding to a ratio of the first signal and the second signal and correlate the ratio with the pressure signal; and
   a housing configured to receive the first condensation particle counter and the second condensation particle counter, the differential pressure sensor, the processor, and the memory.

2. The system of claim 1 further including an accelerometer coupled to the housing, the accelerometer configured to provide an acceleration signal corresponding to sensed acceleration, and wherein the processor is configured to receive the acceleration signal.

3. The system of claim 2 wherein the accelerometer is sensitive to acceleration in three dimensions.

4. The system of claim 2 wherein the processor is configured to correlate the acceleration signal with the ratio.

5. The system of claim 1 wherein the wick includes materials selected from Nylon, high-density polyethylene resin (HDPE), low-density polyethylene resin (LDPE), polyethylene, stainless steel, sintered material, ceramic, polyvinylidene fluoride (PVDF), nitrocellulose, polytetrafluoroethylene (PTFE), or hydrophilic material.

6. The system of claim 1 further including a thermal unit coupled to both the first condensation particle counter and the second condensation particle counter.

7. The system of claim 1 in which the housing is devoid of a reservoir.

8. The system of claim 1 further including a wireless transceiver coupled to the processor.

9. The system of claim 1 further including a battery coupled to the processor and carried by the housing.

10. The system of claim 1 wherein the processor is configured to calculate a protection factor.

11. The system of claim 1 further including a display affixed to the housing and configured to depict the ration.

12. The system of claim 1 wherein the first inlet port is configured to couple with a first end of a first tube, the first tube having a second end coupled to a respiratory mask.

13. The system of claim 12 wherein the second inlet port is configured to couple with a first end of a second tube, the second tube having a second end terminating proximate the respiratory mask.

\* \* \* \* \*